(12) United States Patent
Platzek et al.

(10) Patent No.: US 10,793,532 B2
(45) Date of Patent: Oct. 6, 2020

(54) METHOD FOR PRODUCING THE CRYSTALLINE FORM OF MODIFICATION A OF CALCOBUTROL

(71) Applicant: BAYER PHARMA AKTIENGESELLSCHAFT, Berlin (DE)

(72) Inventors: Johannes Platzek, Berlin (DE); Wilhelm Trentmann, Münster (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/336,217

(22) PCT Filed: Sep. 11, 2017

(86) PCT No.: PCT/EP2017/072683
§ 371 (c)(1),
(2) Date: Mar. 25, 2019

(87) PCT Pub. No.: WO2018/059914
PCT Pub. Date: Apr. 5, 2018

(65) Prior Publication Data
US 2019/0210979 A1    Jul. 11, 2019

(30) Foreign Application Priority Data
Sep. 27, 2016 (EP) .................................. 16190812

(51) Int. Cl.
*C07D 257/02* (2006.01)

(52) U.S. Cl.
CPC ........ *C07D 257/02* (2013.01); *C07B 2200/13* (2013.01)

(58) Field of Classification Search
CPC .......................... C07D 275/02; C07B 2200/13
USPC ....................................................... 540/474
See application file for complete search history.

(56) References Cited

U.S. PATENT DOCUMENTS

| | | |
|---|---|---|
| 4,062,934 A | 12/1977 | Tilly et al. |
| 4,284,620 A | 8/1981 | Lin et al. |
| 4,439,613 A | 3/1984 | Sovak et al. |
| 4,547,357 A | 10/1985 | Pfeiffer et al. |
| 4,885,363 A | 12/1989 | Tweedle et al. |
| 5,059,412 A | 10/1991 | Simon et al. |
| 5,064,633 A | 11/1991 | Simon et al. |
| 5,277,895 A | 1/1994 | Platzek et al. |
| 5,358,704 A | 10/1994 | Desreux et al. |
| 5,386,028 A | 1/1995 | Tilstam et al. |
| 5,410,043 A | 4/1995 | Platzek et al. |
| 5,474,756 A | 12/1995 | Tweedle et al. |
| 5,595,714 A | 1/1997 | Ripa et al. |
| 5,674,470 A | 10/1997 | Tweedle et al. |
| 5,747,000 A | 5/1998 | Platzek et al. |
| 5,980,864 A | 11/1999 | Platzek et al. |
| 5,994,536 A | 11/1999 | Petrov et al. |
| 9,447,053 B2 | 9/2016 | Platzek et al. |
| 2010/0226943 A1 | 9/2010 | Brennan et al. |

FOREIGN PATENT DOCUMENTS

| | | |
|---|---|---|
| AU | 604249 B2 | 12/1990 |
| CA | 1341176 C | 1/2001 |
| EP | 0255471 A1 | 2/1988 |
| EP | 0448181 A2 | 9/1991 |
| EP | 0448191 B1 | 6/1995 |
| EP | 0270483 B2 | 2/1996 |
| EP | 0743283 A2 | 11/1996 |
| EP | 0596586 B1 | 1/1997 |
| EP | 0643705 B1 | 3/1999 |

(Continued)

OTHER PUBLICATIONS

Synthesis and Structure of a New Macrocycicic Polyhydroxylated Gadolinium Chelate used as a contrast agent for magnetic resonance imaging., J. Platzek et al (Year: 1997).*

(Continued)

*Primary Examiner* — Rita J Desai
(74) *Attorney, Agent, or Firm* — Joseph L. Kent; David Schramm; James R. Stevenson

(57) ABSTRACT

A method is described for production of a high purity compound of the formula (I) in crystalline form of the modification A. In this, starting from high purity gadobutrol, the gadolinium is removed by decomplexation with oxalic acid, and then with a calcium salt the calcium complex is produced in high purity. During the crystallization, a water equivalent of 9-11 weight % is set. The crystalline form of the modification A of the compound of the formula (I) is used in the production of Gadovist.

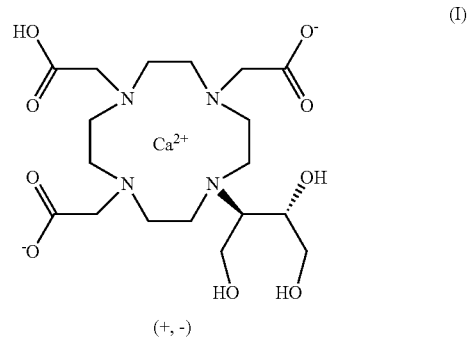

8 Claims, 6 Drawing Sheets

(56) References Cited

FOREIGN PATENT DOCUMENTS

| | | | |
|---|---|---|---|
| EP | 0986548 B1 | 7/2003 | |
| WO | 2011054827 A1 | 5/2011 | |
| WO | WO-2011054827 A1 * | 5/2011 | ........... C07D 257/02 |
| WO | 2012143355 A1 | 10/2012 | |
| WO | WO-2012143355 A1 * | 10/2012 | .............. C07F 5/003 |
| WO | 2016043462 A2 | 3/2016 | |

OTHER PUBLICATIONS

Cacheris; et al., "The Relationship Between Thermodynamics and the Toxicity of Gadolinium Complexes", Magnetic Resonance Imaging, 1990, vol. 8, No. 4.

Caira; Mino R., "Crystalline Polymorphism of Organic Compounds", Topics in Current Chemistry, 1998, 198.

"Diffraction and the X-Ray Powder Diffractometer" B. Fultz et al. Transmission Electron Microscopy and Diffractometry of MaterialsGraduate Texts in Physics. Springer-verlag Berlin Heidelberg 2013.

Formanovsky A.A. et al., "One-Stage Monosubstitution in Cyclen—Two Novel Examples", Synthetic Communications, 1996, 26(8), 1595-1603.

"Impurity Profiling: Theory and Practice", P. Venkatesan et al./J. Pharm. Sci. & Res. vol. 6(7), 2014254-259.

"International Preliminary Report on Patentability from PCT Application No. PCT/EP2010/066655", dated May 8, 2012.

"International Preliminary Report on Patentability from PCT Application No. PCT/EP2017-072683", dated Apr. 11, 2019.

"International Search Report and Written Opinion for International Patent Application Publication PCT/EP2010/066655.", dated Dec. 22, 2010.

Karl-Olof Lovblad., "Gadovist in Multiple Sclerosis", Touch Briefings, Department of Neuroradiology, Geneva University Hospital, 2008.

Platzek et al.,, "Synthesis and Structure of a New Macrocyclic Polyhydroxylated Gadolinium Chelate Used as a Contrast Agent for Magnetic Resonance Imaging", Inorg. Chem., 1997, vol. 36 No. 26, 6086-6093.

Product Specification for Gadovist, Gadovist 1.02005.

Toth; et al., "Equilibrium and Kinetic Studies on Complexes of 10[2,3-dihydroxy-(1-hydroxymethyl)-propl]1,3,7,10-tetraazacyclododecane-1,4,7-triacetate", Inorganica Chimia Acta 246, 1996, 191-199.

* cited by examiner

METHOD FOR PRODUCING THE CRYSTALLINE FORM OF MODIFICATION A OF CALCOBUTROL

CROSS REFERENCE TO RELATED APPLICATIONS

The present application is a U.S. national stage filing under 35 U.S.C. § 371 of International Application No. PCT/EP2017/072683, filed 11 Sep. 2017, which claims priority to European Patent Application No. EP 16190812.4, filed 27 Sep. 2016, the disclosures of each of which are incorporated in their entirety herein by this reference.

FIELD OF THE DISCLOSURE

The invention relates to a method for producing the crystalline form of modification A of the calcium complex of dihydroxy-hydroxy-methylpropyl-tetraazacyclododecane-triacetic acid (calcobutrol) of the formula (I)

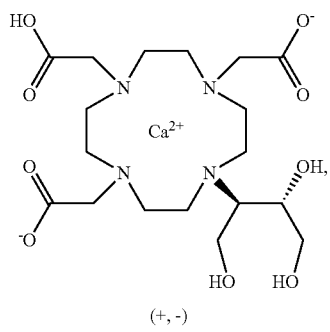

(I)

(+, -)

and the use of the crystalline modification A of the calcium complex of dihydroxy-hydroxy-methylpropyl-tetraazacyclododecane-triacetic acid (calcobutrol) of the formula (I) for the production of galenical formulations of gadobutrol.

BACKGROUND

Calcobutrol is an additive in the galenical formulations of gadobutrol and has the task of preventing release of gadolinium in the formulation (solutions). The production of high purity calcobutrol is described in WO 2011/054827 A1 (Bayer AG) and in WO 2016/043462 A2 (ST PHARM CO., LTD.):

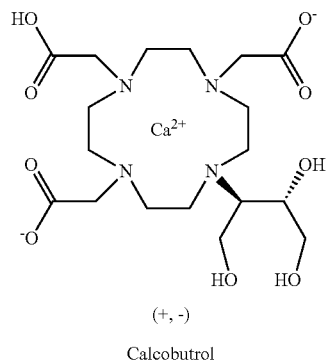

(+, -)

Calcobutrol

Gadobutrol is a gadolinium-containing contrast medium for nuclear spin tomography and since 2000 has been approved in Germany as Gadovist® in the indication "Contrast enhancement in cranial and spinal magnetic resonance tomography (MRT)" (EP 0448191 B1, EP 0643705 B1, EP 0986548 B1, EP 0596586 B1 and CA Patent 1341176). The production of high purity gadobutrol is described in the patent application WO 2012/143355 A1. It is a nonionic complex, consisting of gadolinium(III) and the macrocyclic ligand dihydroxy-hydroxy-methylpropyl-tetraazacyclododecane-triacetic acid (butrol).

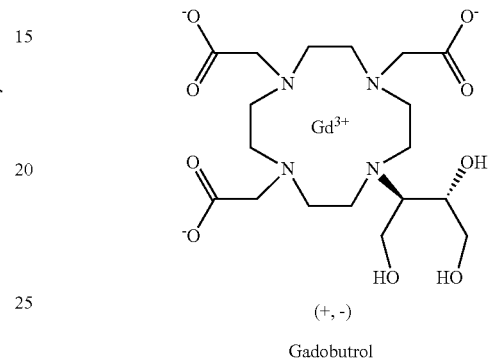

(+, -)

Gadobutrol

Gadovist is sold as a 1 molar aqueous solution, which consists of the following components in the formulation: gadobutrol, calcobutrol sodium salt, trometamol, hydrochloric acid and water for injection.

With most gadolinium-containing contrast media, it has been found advantageous to use an excess of the gadolinium complexing ligand in the form of the calcium complex in the formulation, EP 0 270 483 B2. This has essentially the task of preventing release of gadolinium in the formulation (e.g. on multiyear storage or recomplexation with foreign ions from the glass).

The synthesis of the calcium complex (calcobutrol) is described in Inorg. Chem 1997, 36, 6086-6093. For this, complexation of the butrol ligand in water is performed with calcium carbonate, the aqueous solution is then freeze-dried and the residual powder boiled down as a suspension in 26-fold ethanol, this is not a crystallization process, but rather a hot extractive stirring of a suspension. However, the process described there did not yield the high purity required by the authorities, for during the boiling down in pure ethanol the occurrence of new impurities is to a significant extent observed, with these also being, among other impurities, also the two ethyl esters A1 and B1, and the ligand esters C2 and D2:

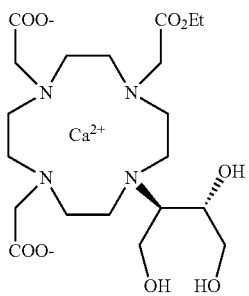

A1

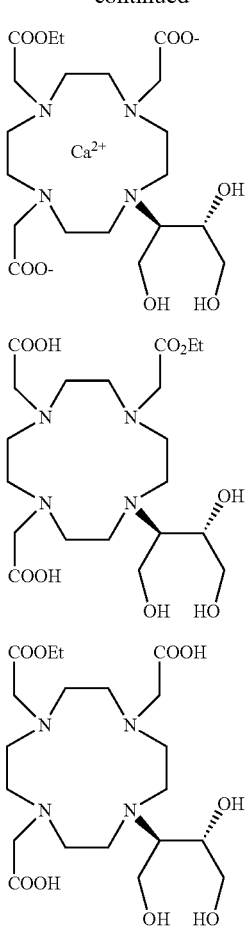

Only a material with a purity of ca. 94% (100% method, HPLC) could be obtained, since these two ethyl esters also crystallize out in pure ethanol. The ligand obtainable from the gadobutrol synthesis (butrol) does not have the high purity necessary for it to be directly converted into the calcium complex. Because of its highly zwitterionic nature, a further purification of the ligand is difficult and costly.

The decomplexation of gadolinium complexes with oxalic acid with addition of a mineral acid (mostly hydrochloric acid) is described in the literature, see for example Inorganica Chimica Acta 249 (1996), 191-199. Here the production of high purity ligand is outlined, in that the product is finally stirred out of methanol at room temperature, in order thereby to create a high purity ligand for the stability constant determination. However the method described there is not suitable for scale-up and also does not disclose the production, isolation and purification of calcobutrol. Thus in US PS 5595714 it is disclosed that on the one hand gadolinium, and also free ligands, can be recovered from the gadolinium-containing contrast media by decomplexation with oxalic acid/hydrochloric acid. However, the utilization of the method for the production of calcium salts is not mentioned within this document.

While the neutral gadolinium complex (gadobutrol) can be purified on ion exchangers, and in conclusion can be obtained at high purities (>>99%) by a very effective crystallization, this is not possible with calcobutrol because of the additional acid function. A purification of the complex did not succeed, since, even with preparative HPLC, impurities coming very close to the main peak could not be removed.

BRIEF SUMMARY

The purpose of the present invention is reproducibly to obtain very pure calcobutrol with a stable, defined polymorphic form. The difficulty in all purification methods essentially consists in on the one hand reproducibly obtaining high purity, and also 1:1 Ca:ligand stoichiometry. Calcobutrol is only stable under neutral conditions and during any purification operation, whether this be chromatography or ion exchanger treatment, always loses significant proportions of calcium through decomplexation.

DETAILED DESCRIPTION

Figure 1:
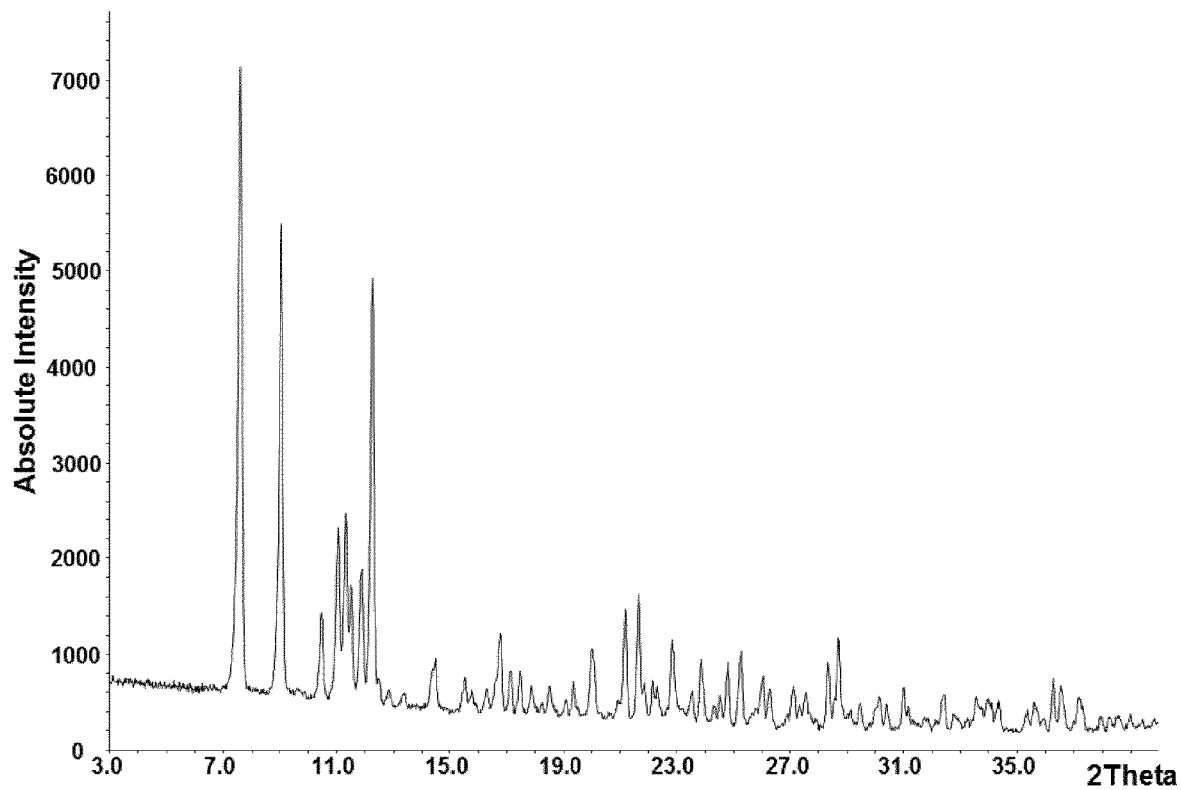
FIG. 1 shows the x-ray powder diffraction diagram of the modification A from batch No. 16.

With the present invention a very efficient method has been found, which makes it possible to fulfil the aforesaid requirements.

In the patent specification WO 2011/054827 A1 (Bayer AG), it was surprisingly found that efficient production is possible by starting from high purity gadobutrol, as for example described in WO 2012/143355 A1. The gadolinium is removed from the complex gadobutrol by decomplexation, the ligand thereby obtained in very high purity and then complexed with calcium 2+ ions. In WO 2011/054827 A1 (Bayer AG) a crystallization from aqueous ethanol is described as an example, wherein crystallization was performed from aqueous ethanol, which yields very pure calcobutrol.

It was now surprisingly found that the water equivalent of the ethanolic solution must lie in a range of 9% and 11%, in order reproducibly to produce one specific modification (target modification A). This is different to the methods published before (Inorganic Chemistry 1997, 36, 6086-6093 and WO 2011/054827 A1), in which no special attempts were made to control the water content during the crystallization process. The crude distillation down to an undefined target quantity of butrol ligands used (as is described in the prior art) is in particular only a crude guide value for the further improvement of the robustness of the process and can by far not compete with a robust in-process control for water; thus this value can relatively simply be brought into the desired range of 9-11% by further addition of ethanol or water. Furthermore, it has been found advantageous if after complexation with calcium carbonate has been effected the 1:1 stoichiometry in Ca:butrol is again checked by means of an in-process control and optionally further adjusted by addition of small quantities of calcium carbonate or butrol, so that an exactly 1:1 stoichiometry is obtained. Surprisingly, it could be observed here that even the smallest deviations from this stoichiometry have effects on the purity and the polymorphic form produced. The reproducible production succeeds only with the novel inventive method. This is on the one hand important since among the four polymorphic forms (modifications) A, B, C and D found, only form A (modification A) has good storage stability, while B, C and D to a large extent tend to be hygroscopic, which causes considerable problems in the production of the pharmaceutical formulation (Gadovist®). Strong hygroscopicity is always a problem in pharmacy during the storage and weighing out of bulk quantities.

The four polymorphic forms mentioned are the polymorphic modifications A, B, C and D. These exhibit the properties shown in Table 1:

TABLE 1

| Modification | Composition | Solubility in water (g/L) |
|---|---|---|
| A | mixed solvate with 1 mol water and 1/5-1/4 mol ethanol | >500 |
| B | dihydrate | >500 |
| C | dihydrate | >500 |
| D | dihydrate | >500 |

On storage under conditions of high atmospheric humidity, all four modifications convert into amorphous substance. Modification B, C and D can for example be obtained by crystallization from water with elevated water equivalents >12%.

By means of the novel process, it was possible to solve the problem of the hygroscopicity, in that the crystallization is performed from aqueous ethanol while maintaining the water equivalent between 9% and 11%. Astonishingly, it was found that by operating at water equivalents of 9-11% the content of the ethyl esters A1, B1, C2 and D2 described above decreases massively, since firstly the esterification is strongly inhibited and secondly these esters are better soluble in aqueous ethanol than in pure ethanol, which is relatively astonishing to those skilled in the art. In the final product, these esters are no longer to be found (below the detection limit of the method).

In the practical implementation, butrol is complexed with calcium carbonate preferably at 20-30° C. In this temperature range, excessive foaming is suppressed. The stoichiometry is then analysed by means of an in-process control for Ca and butrol, and optionally adjusted to exactly 1:1 by addition of a correcting quantity of calcium carbonate or butrol. The mixture is then concentrated as described in WO 2011/054827 A1 (Bayer AG), i.e. water is distilled off under vacuum, however to a defined final volume based on 7-8 times the quantity of calcium carbonate used. After this, ca. 26 times the quantity of ethanol (e.g. also denatured with MEK=methyl ethyl ketone) is metered in over 60 to 70 minutes at boiling temperature, and after cooling to 20° C. the water equivalent is determined by means of an in-process control. By addition of a correcting quantity of ethanol or methanol, the water equivalent is readjusted until it lies within the target corridor of 9-11%. Advantageously, a value of ca. 10% is set. Next, the mixture is heated for 3 hours under reflux. This procedure also allows the use of normal commercial alcohol, denatured for example with toluene, methyl ethyl ketone, hexane or thiophene.

At water equivalents<9%, impurities already crystallize out as well, so that some batches are outside the specification. Moreover, amorphous fractions then arise to an increased extent in the polymorph A. At water equivalents>11%, very clean products are admittedly obtained, but the yield falls relatively abruptly, since then the solubility of calcobutrol is too high and the crystallization is impeded, moreover the formation of polymorphic forms B, C and D is preferentially observed. With use of a water equivalent in the range of 9-11%, on the one hand the yield is very good, which from the economic viewpoint is of great interest, and on the other hand, the quality of the polymorph (modification A) is very high. Operating with water equivalents in the range of 9-11% guarantees reproducible, robust and scalable operation of the process, which can now be scaled up as desired. The new process is very simple to manage, since it requires only the measurement of the water equivalent via a simple in-process control. This in-process control can for example be effected by a Karl Fischer titration or also by a comparable other method. The course of the operation is not materially affected by the in-process control, since the result can be determined relatively quickly.

A further advantage of the novel process according to the invention is the already mentioned reproducible production of a defined polymorph (for the characterization of the polymorphic forms, see examples).

The invention essentially comprises a method for producing the calcium complex of dihydroxy-hydroxy-methylpropyl-tetraazacyclododecane-triacetic acid (calcobutrol), wherein it is complexed with calcium$^{2+}$ ions in water, and then crystallized from ethanol, wherein the water content (water equivalent) (Karl Fischer) advantageously lies in a range of 9-11%, in order to obtain the desired target polymorph (modification A).

Table 2 shows the water and ethanol content of three typical production batches (24, 25, 26), for which the crystalline form was determined via XRPD (Xray powder diffractometry). These three batches resulted in the polymorphic form A (modification A). Table 2 also shows the properties of two additional batches which have been prepared according to published procedures (Example 5: Inorganic Chemistry 1997, 36, 6086-6093 and Example 6: WO 2011/054827 A1).

The batches according to Examples 5 and 6 are characterized by their significantly low water content and their extremely low ethanol content, both of which clearly indicating that these batches do not correspond to the polymorphic form A (Modification A). These findings are confirmed by comparison of the corresponding XRPD spectra which show totally different reflex patterns.

TABLE 2

| Batch-No. | Modification | Water content (weight %) | Ethanol content (weight %) |
|---|---|---|---|
| 24 | A | 4.27 | 2.18 |
| 25 | A | 4.39 | 2.08 |

TABLE 2-continued

| Batch-No. | Modification | Water content (weight %) | Ethanol content (weight %) |
|---|---|---|---|
| 26 | A | 4.41 | 2.06 |
| Example 5 | * | 3.47 | 610 ppm |
| Example 6 | * | 2.54 | 200 ppm |

*a modification which is different from modification A

For comparison, the theoretical contents of water and ethanol for the modification A are used:
Modification A=calcobutrol*1H$_2$O*1/5 ethanol
Weight % water: 4.23
Weight % ethanol: 2.16

Specifically, the invention also contains the process parameters for the crystallization of the calcium complex of dihydroxy-hydroxy-methylpropyl-tetraazacyclododecane-triacetic acid, wherein it is firstly complexed employing very mild conditions with calcium$^{2+}$ ions at 20-25° C. (this is an important difference to the state of the art, where the complexation is performed at significant higher temperature (80-90° C.)), after completion of the reaction the stoichiometry in Ca:butrol is readjusted by means of an in-process control and optionally by a corrective measure such as the addition of calcium carbonate or butrol, then the product is crystallized from aqueous ethanol, preferably with a water content (water equivalent) of 9-11%, and after isolation then dried under vacuum.

As suitable calcium$^{2+}$ ion sources for the complexation, calcium carbonate, calcium oxide or calcium hydroxide have been found. This complexation preferably proceeds in aqueous solution at various temperatures from 20-90° C. However, with calcium carbonate, complexation can already be effected particularly mildly at 20-30° C.

The final conversion to calcobutrol is performed by complexing butrol with stoichiometric quantity of calcium carbonate in water. However, calcium oxide (CaO) or calcium hydroxide Ca(OH)$_2$ can also be used. Preferably calcium carbonate (CaCO$_3$) is used.

For particle removal and microbe reduction, the mixture is treated with activated charcoal and this is filtered off. The filtrate is substantially concentrated under vacuum and by addition of ethanol the in-process control for water performed, optionally readjusted and then brought to crystallization. For this, it is heated under reflux, and finally cooled. The crystalline product deposited is filtered off and then washed with a little ethanol. It is then dried (to constant weight) in the vacuum cabinet.

The calcobutrol of modification A produced in this manner is characterized by very high quality. The product is colourlessly soluble in water and has a purity of >99.0%, with production lots in production the purities typically lie at 99.7% (purity by 100% method, HPLC). The overall process, starting from gadobutrol to calcobutrol is characterized by high reproducibility and efficiency. The overall yield (over two steps) is therefore very good. The product is storage-stable and can be used in the pharmacy for the formulation production of the Gadovist solution. The sodium salt of calcobutrol is generated in situ by addition of a stoichiometric quantity of sodium hydroxide solution. Solutions of Gadovist prepared in this manner are storage stable for several years and guarantee the security that free toxic gadolinium never gets into the solution.

It is thus possible to meet the desire of the authorities and pharmacists inexpensively to provide a calcobutrol of high purity and defined polymorphic form (modification A), which is directly suitable for further processing and the production of Gadovist.

The manufacturing process as described and claimed herein leads to the stable and uniform Calcobutrol of polymorphic form A (modification A) in a reliable manner. Formerly potential different forms should be avoided in order to comply with increasing regulatory and GMP requirements.

Different polymorphic forms even for a pharmaceutical excipient include the risk of minor insoluble solid residues, which have been actually observed in the past. To avoid the risk for parenteral use a uniform fully soluble polymorph A Calcobutrol should be used only.

Moreover, different polymorphic forms lead also to different XRPD and infrared spectra, which should be avoided to have a clear conformity of the identity, which is an essential test for pharmaceutical use.

Although the structure of Calcobutrol is already known, the polymorphic form A is unique for the usage in parenteral drug products and described herein in detail for the first time.

The invention also comprises use of the polymorph A of the calcium complex of dihydroxy-hydroxy-methylpropyl-tetraazacyclododecane-triacetic acid for the production of the normal commercial galenical formulations of gadobutrol.

A subject of the present invention is the compound of the formula (I) in the crystalline form of modification A

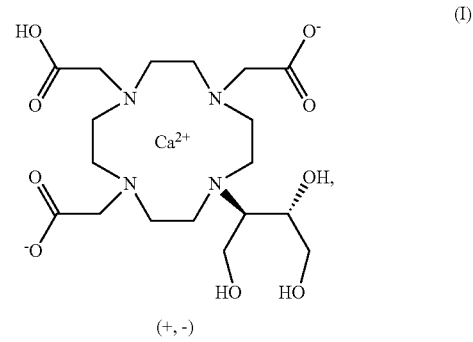

wherein x-ray powder diffraction diagram of the compound shows peak maxima of the 2 theta angle at 7.6°, 9.1°, 11.1°, 11.3°, 11.9° and 12.3°.

A further subject of the present invention is the compound of the formula (I) in crystalline form of the modification A, wherein it is a monohydrate with 2.0-2.5 weight % ethanol.

A further subject of the present invention is the compound of the formula (I) in crystalline form of the modification A, wherein it is a monohydrate with 2.0-2.2 weight % ethanol.

A further subject of the present invention is the compound of the formula (I) in crystalline form of the modification A, wherein it is a monohydrate with 2.0-2.5 weight % ethanol and wherein the x-ray powder diffraction diagram of the compound shows peak maxima of the 2 theta angle at 7.6°, 9.1°, 11.1°, 11.3°, 11.9° and 12.3°.

A further subject of the present invention is the compound of the formula (I) in crystalline form of the modification A, wherein it is a monohydrate with 2.0-2.2 weight % ethanol and wherein the x-ray powder diffraction diagram of the compound shows peak maxima of the 2 theta angle at 7.6°, 9.1°, 11.1°, 11.3°, 11.9° and 12.3°.

A further subject of the present invention is a method for producing the compound of the formula (I) in crystalline form of the modification A, wherein the gadolinium complex of dihydroxy-hydroxy-methylpropyl-tetraazacyclodo-decane-triacetic acid (gadobutrol) is decomplexed, the precipitated gadolinium salt is removed, then the solution with the free ligands is bound to an acidic ion exchanger, then eluted with aqueous basic solution, then complexed with calcium$^{2+}$ ions, then the Ca:butrol stoichiometry is adjusted to 1:1 by means of an in-process control, then crystallized from aqueous ethanol with a water content of 9-11 weight % water by means of an in-process control for the determination of water and the product is then dried and thus the compound of the formula (I) is isolated in crystalline form of the modification A.

A further subject of the present invention is a method for producing the compound of the formula (I) in crystalline form of the modification A, wherein the gadolinium complex of dihydroxy-hydroxy-methylpropyl-tetraazacyclodo-decane-triacetic acid (gadobutrol) with oxalic acid in water is decomplexed hot, the precipitated gadolinium oxalate is filtered off, then the free ligand is bound to an acidic ion exchanger, then eluted with aqueous ammonia solution, after concentration of the solution complexed with calcium$^{2+}$ ions, then by means of an in-process control the Ca:butrol stoichiometry is adjusted to 1:1, then is heated under reflux from aqueous ethanol with a water content of 9-11 weight % water, dried under vacuum after isolation, and thus the compound of the formula (I) is isolated in crystalline form of the modification A.

A further subject of the present invention is a method for producing the compound of the formula (I) in crystalline form of the modification A, wherein calcium carbonate, calcium oxide or calcium hydroxide is used for the complexation.

A further subject of the present invention is a method for producing the compound of the formula (I) in crystalline form of the modification A, wherein calcium carbonate is used for the complexation.

A further subject of the present invention is a method for producing the compound of the formula (I) in crystalline form of the modification A, characterized in that calcium carbonate is used for the complexation and that the complexation is performed in a temperature range of $\geq 0°$ C. and $\leq 50°$ C.

A further subject of the present invention is a method for producing the compound of the formula (I) in crystalline form of the modification A, characterized in that calcium carbonate is used for the complexation and that the complexation is performed in a temperature range of $\geq 10°$ C. and $\leq 40°$ C.

A further subject of the present invention is a method for producing the compound of the formula (I) in crystalline form of the modification A, characterized in that calcium carbonate is used for the complexation and that the complexation is performed in a temperature range of $\geq 15°$ C. and $\leq 35°$ C.

A further subject of the present invention is a method for producing the compound of the formula (I) in crystalline form of the modification A, characterized in that calcium carbonate is used for the complexation and that the complexation is performed in a temperature range of $\geq 20°$ C. and $\leq 30°$ C.

A further subject of the present invention is a method for producing the compound of the formula (I) in crystalline form of the modification A, characterized in that calcium carbonate is used for the complexation and that the complexation is performed in a temperature range of $\geq 20°$ C. and $\leq 25°$ C.

A further subject of the present invention is a method for producing the compound of the formula (I) in crystalline form of the modification A, wherein the stoichiometry in calcium:butrol is adjusted to 1:1.

A further subject of the present invention is a method for producing the compound of the formula (I) in crystalline form of the modification A, wherein by means of an in-process control the water equivalent during the crystallization is set in a range von 9-11%.

A further subject of the present invention is the compound of the formula (I) in crystalline form of the modification A, wherein the compound is produced by a process mentioned as a subject of the present invention.

A further subject of the present invention is the compound of the formula (I) in crystalline form of the modification A, wherein the purity is $\geq 99.0\%$.

A further subject of the present invention is the compound of the formula (I) in crystalline form of the modification A, wherein the purity is $\geq 99.6\%$.

A further subject of the present invention is the compound of the formula (I) in crystalline form of the modification A, wherein the purity is $\geq 99.7\%$.

A further subject of the present invention is use of the compound of the formula (I) in crystalline form of the modification A for the production of galenical formulations of gadobutrol.

The following examples serve to describe the subject of the invention.

EXPERIMENTAL SECTION

Example 1

General production procedure for calcobutrol by means of in-process control for water during the crystallization 2 kg of gadobutrol together with 0.8 kg of oxalic acid dihydrate were suspended in 14 L water and stirred for at least 3 hours at 80° C. (normally 3 to 5 hours). This was allowed to cool to 20° C. and further stirred for 60 minutes at 20° C. The gadolinium oxalate precipitated was filtered off and rinsed twice with 3 L water each time (~20 L ion exchanger eluate). An ion exchange column filled with cation exchange resin Amberlite 252 C was flushed with water until the eluate had reached a conductivity of <10 µS/cm (target pH>4.5 and <5.5). In this case a pH of pH 4.73 and a conductivity of 4.42 µS/cm were found. The aforesaid ion exchanger eluate (ca. 20 L) was fed onto the ion exchange column (feed rate 250-350 mL/min). This was then washed with 15 L water until the conductivity of the eluate was <5 µS/cm (measured values were pH 4.48 and 4.99 µS/cm). The ion exchange column was then slowly washed with a 1.4-1.7% aqueous ammonia solution (a 1.4% solution was used). The product-containing eluate fractions were collected (pH 11.01). The eluate was concentrated under vacuum at 64.4° C. until the solution had reached a density of 1.07 g/mL. 7.906 kg of a solution of pH 3.8 were obtained. A 127.13 g sample had previously been taken in order to determine pH, density and the butrol ligand content. After withdrawal of the sample, 7.7795 kg of solution remained with a butrol ligand content of 18.99% (measurement against external standard), which corresponded to a mass of 1.477 kg butrol. For the complexation with calcium, 328 g of calcium carbonate were added and then rinsed with 1019.7 g water. This was left stirring for 60 minutes at 23° C. (during which the calcium carbonate dissolved). Next an in-process control for excess calcium or excess butrol is performed. Excess calcium was complexed by further addition of the corresponding quantity of ligand, similarly, in case of an excess of butrol ligand, a corresponding quantity of calcium carbonate was added, until the stoichiometry Ca:butrol is 1:1. After this, 120.03 g of activated carbon NORIT SX PLUS, 20 µs was added and with rinsing with 91.6 g water. This was stirred for 60 minutes at 23° C., then the activated carbon was filtered off and rinsed with 0.4 L water. The filtrate was filtered through a sterile filter Sartopore 2 mini cartridge 0.2 µm (9.3537 kg of solution were obtained). Then water was distilled off at 75 mbar and 70° C. water to ca. 7 to 8-fold based on the quantity of calcium carbonate used (328 g of calcium carbonate were used, that means distillation was performed to a final quantity of 2296 g to 2624 g). Overall, 6755.5 g water were distilled off, which corresponded to a quantity of final volume calcobutrol solution of ca. 7.9-fold based on calcium carbonate. The mixture was heated to reflux and 8556.9 g ethanol, MEK (methyl ethyl ketone)-denatured, were metered into it over 60 minutes (ca. 26-fold quantity based on quantity of calcium carbonate used). It is allowed to cool to 23° C. and an in-process control of the water equivalent is performed according to Karl Fischer. The water equivalent at this point must be 9 and 11 weight %, and as far as possible the ideal value should lie at 10 weight % (in any case however in this range of 9-11 weight %). If the value deviates from this window, water (in case of <9 weight %), or ethanol, MEK-denatured (in case of >11 weight %) as appropriate must be added. A water content of 9.24 weight % was found and processing was continued. For this, the mixture was heated for 3 hours under reflux, then cooled (gradient) over 14 hours to 20° C. and the crystallized mixture stirred for a further 60 minutes. The crystallization product deposited was filtered off, then washed in 2 portions with a total of 812 g ethanol, MEK-denatured. The filter cake was placed on a rack in a clean-room and then dried (to constant weight, 20-85 hrs). After drying, 1264.9 g of product were obtained, which corresponds to a typical production batch size.

Example 2

Calcobutrol Production on the Technical Scale

The following table reproduces the results from the production of calcobutrol, which was produced according to the general production procedure analogously to example 1. The average batch size was 1.0-1.2 kg. Table 3 shows the high purity and the high contents which are obtained when the water equivalent is set between 9 and 11 weight %.

TABLE 3

| Batch No. | IPC* water equivalent (KF Karl Fischer, weight %) | Purity (HPLC,%) | Content (%) | Modification according to XRPD# |
|---|---|---|---|---|
| 1 | 10 | 99.7 | 99.8 | A |
| 2 | 10 | 99.7 | 99.6 | A |
| 3 | 10 | 99.7 | 99.4 | A |
| 4 | 10 | 99.7 | 100.2 | A |
| 5 | 9 | 99.7 | 100.4 | A |
| 6 | 9 | 99.7 | 99.2 | A |
| 7 | 10 | 99.7 | 99.9 | A |
| 8 | 10 | 99.7 | 99.9 | A |

TABLE 3-continued

| Batch No. | IPC* water equivalent (KF Karl Fischer, weight %) | Purity (HPLC,%) | Content (%) | Modification according to XRPD# |
|---|---|---|---|---|
| 9 | 10 | 99.7 | 99.7 | A |
| 10 | 10 | 99.7 | 100.1 | A |

*IPC: in-process control
XRPD: Xray powder diffractometry

Example 3

Residual Solvent Contents on Use of Ethanol Denatured with Methyl Ethyl Ketone

The batches described here were produced as described above, and ethanol denatured with methyl ethyl ketone was used. Table 4 shows that the residual solvent limit of 5,000 ppm required by the ICH (International Conference on Harmonisation) Guideline was observed.

TABLE 4

| Batch No. | MEK (methyl ethyl ketone) (ppm) |
|---|---|
| 11 | 306 |
| 12 | 262 |
| 13 | 500 |
| 14 | 555 |

Example 4

Polymorphism

The polymorphs B, C and D are characterized by a high water content and can be produced from polymorph A (modification A) by addition of water 12 weight %) during the crystallization process. Table 5 shows the properties of these polymorphs, which were produced on a small scale in the laboratory.

TABLE 5

| Batch No. | Modification according to XRPD | Water content (weight %) | Ethanol content (weight %) |
|---|---|---|---|
| 15 | A | 4.0 | 2.0 |
| 16 | A | 3.9 | 2.0 |
| 17 | A | 4.3 | 2.1 |
| 18 | A | 4.0 | 2.2 |
| 19 | B | 7.8 | 0.02 |
| 20 | C | 8.2 | 0.01 |
| 21 | C | 7.4 | 0.01 |
| 22 | D | 6.6 | 3.0 |
| 23 | C + B | 6.5 | 0.63 |

FIG. 1 shows the x-ray powder diffraction diagram of the modification A from batch No. 16.

Table 6 shows by way of example three typical production batches (24, 25, 26), in which the polymorphic form was determined by means of XRPD. In all batches, the modification A was reproducibly obtained.

In addition, table 6 shows analytical data for two batches which have been prepared according to procedures described in the prior art (Examples 5 and 6, procedures for preparation and isolation as described below). These batches are characterized by their significantly low water content and their extremely low ethanol content, both of which clearly indicating that these batches do not correspond to the polymorphic form A (Modification A). These findings are confirmed by comparison of the corresponding XRPD spectra (see below).

TABLE 6

| Batch No. | Modification | Water content (weight %) | Ethanol content (weight %) |
|---|---|---|---|
| 24 | A | 4.27 | 2.18 |
| 25 | A | 4.39 | 2.08 |
| 26 | A | 4.41 | 2.06 |
| Example 5 | * | 3.47 | 610 ppm |
| Example 6 | * | 2.54 | 200 ppm |

*a modification which is different from Modification A

Figure 2:
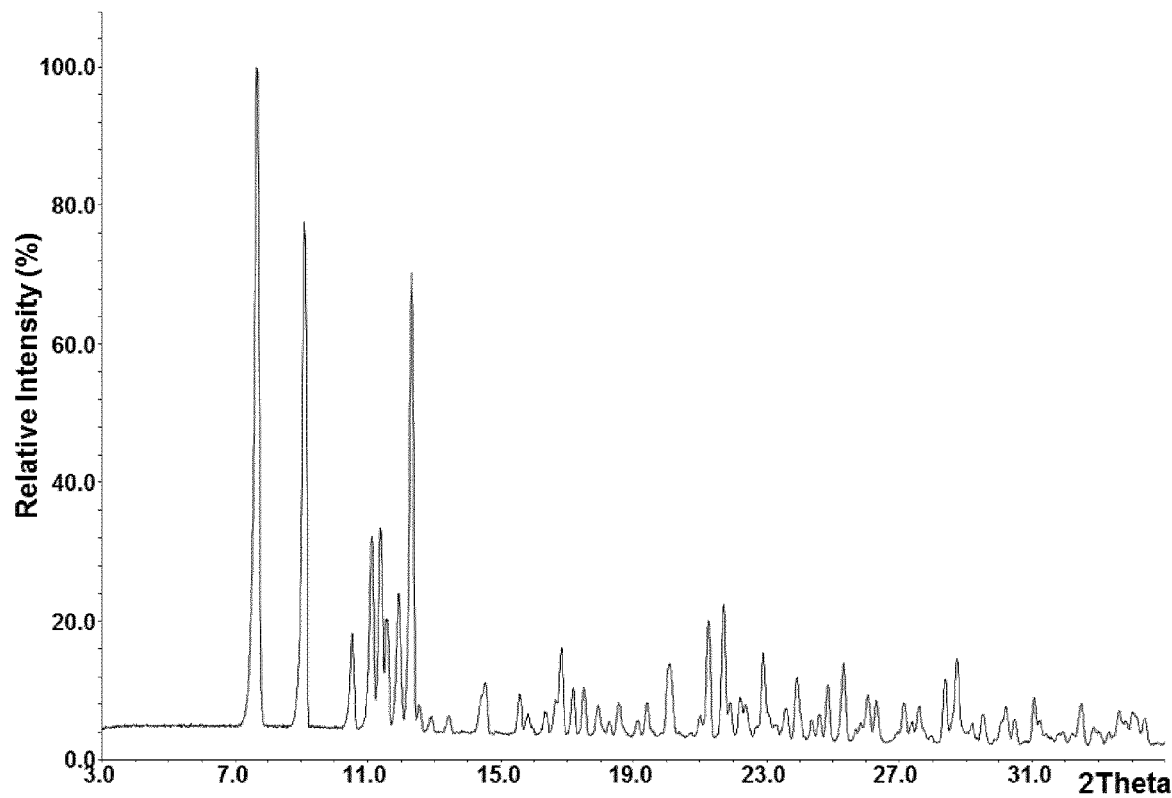
FIG. 2 shows by way of example a diffraction diagram of batch No. 24. The batch corresponds to the modification A.
Figure 3:
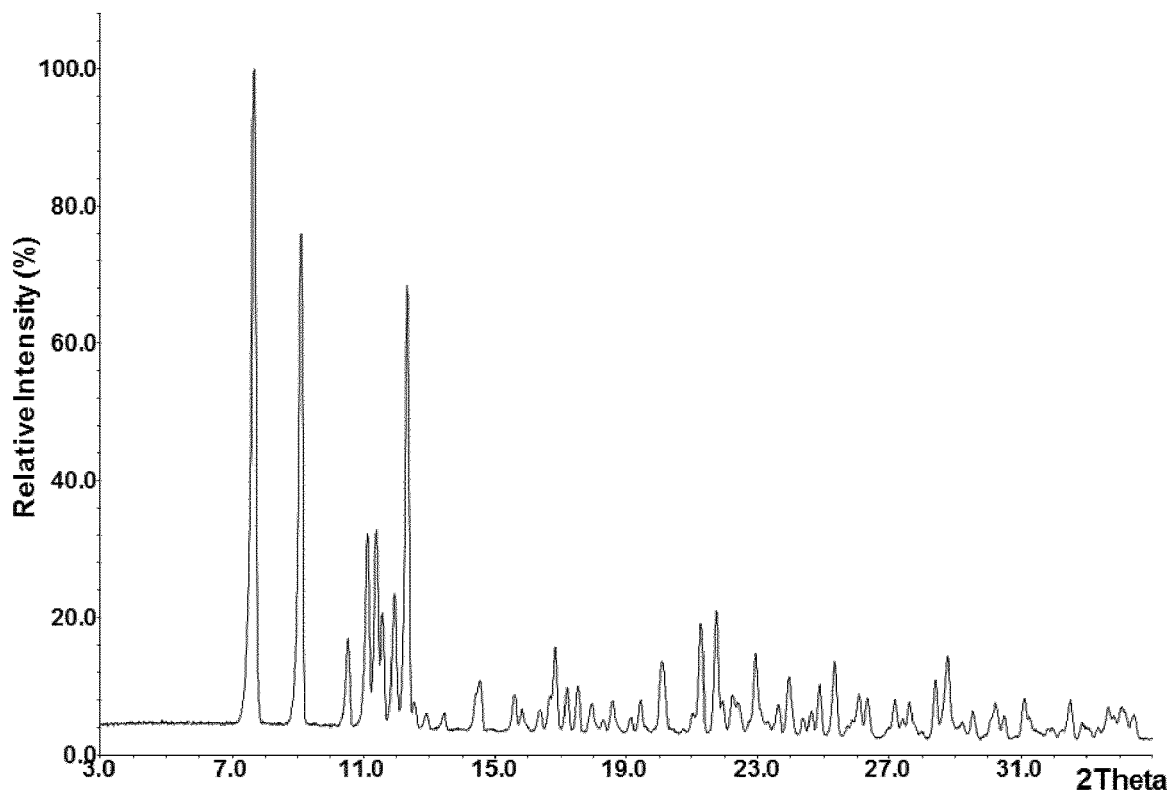
FIG. 3 shows by way of example a diffraction diagram of batch No. 25. The batch corresponds to the modification A.
Figure 4:
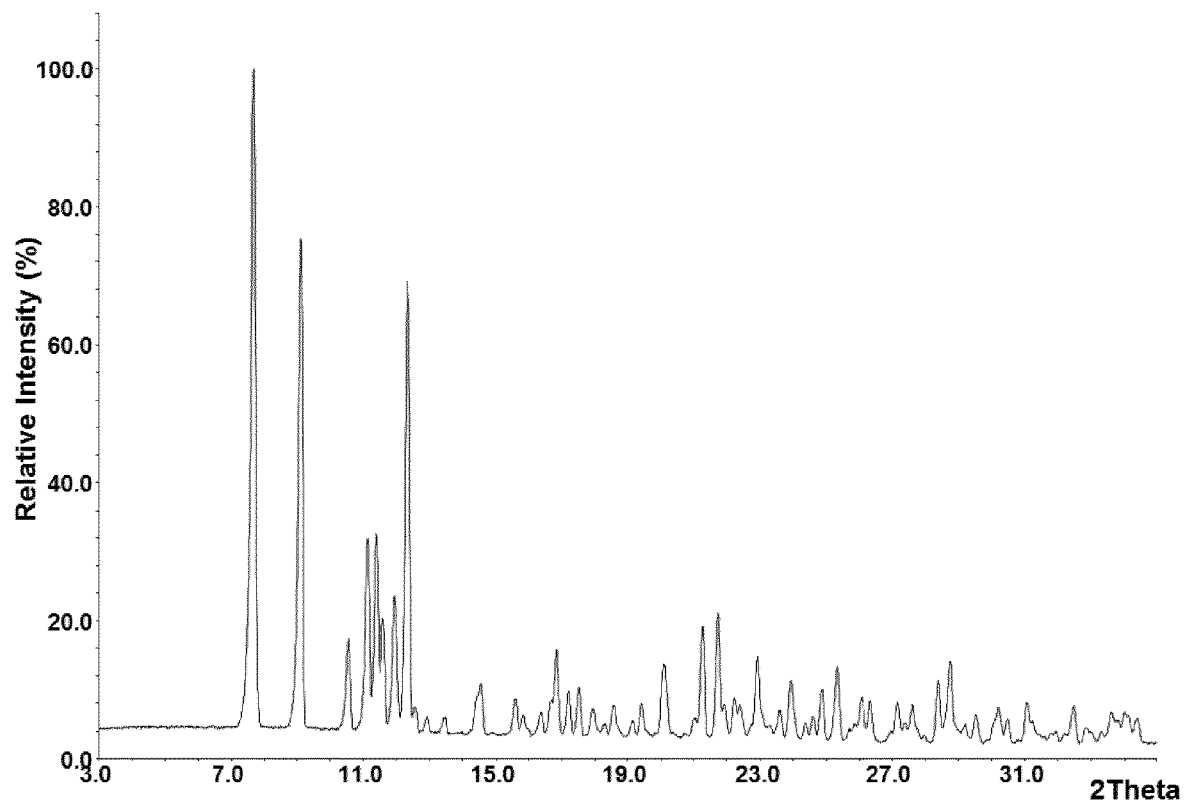
FIG. 4 shows by way of example a diffraction diagram of batch No. 26. The batch corresponds to the modification A.

As the comparison, the theoretical contents of water and ethanol for the modification A are used:
Modification A=calcobutrol*$1H_2O$*1/5 ethanol
Weight % water: 4.23
Weight % ethanol: 2.16
FIGS. 2 (Batch No. 24), 3 (Batch No. 25) and 4 (Batch No. 26) show by way of example three diffraction diagrams. The batches correspond to the form A (modification A).

Table 7 shows the influence of the water equivalent on the modification obtained on crystallization.

TABLE 7

| Batch No. | IPC water equivalent (KF Karl Fischer, weight %) | Modification |
|---|---|---|
| 27 | 10 | A |
| 28 | 9 | A |
| 29 | 11 | A |
| 30 | 12 | D |
| 31 | 12 | D |
| 32 | 13 | B + C |
| 33 | 8 | little A and amorphous fractions |
| 34 | 8 | little A and amorphous fractions |
| 35 | 7 | little A and amorphous fractions |
| 36 | 7 | little A and amorphous fractions |

Batches 33-36: batches in whose production the water equivalent was adjusted to 7-8% are hygroscopic since they contain a higher proportion of amorphous substance.

Xray powder diffractometry of calcobutrol (XRPD)

Table 8 shows 2θ values of the diffraction peaks of calcobutrol of the modification A (batches 16, 24, 25, 26). The peak maxima are found at 2θ angles of 7.6°, 9.1°, 11.1°, 11.3°, 11.9° and 12.3°.

TABLE 8

| Diffraction angles (2θ, °) |
|---|
| 7.6 |
| 9.1 |
| 10.5 |
| 11.1 |
| 11.3 |
| 11.9 |
| 12.3 |
| 14.5 |
| 15.5 |
| 16.8 |
| 17.1 |
| 17.5 |
| 20.0 |
| 21.2 |
| 21.7 |
| 22.2 |
| 22.9 |
| 23.9 |
| 24.8 |
| 25.3 |
| 26.0 |
| 28.3 |
| 28.7 |
| 36.3 |

Instrument Set-Up for XRPD:
Sample preparation: The powder is prepared as a thin layer between two sheets.
Instrument: X-Ray powder diffractometer (STOE STADI P)
Generator: 40 kV/40 mA
Detector: linear position-=sensitive detector
Irradiation: germanium-monochromatized $CuK_{\alpha 1}$ radiation
Technique: Transmission
Scan range: 3° 2θ 35°
Step width: 0.5°
Measurement time: 15 sec/step
Comparison with Prior Art The following examples demonstrate that the polymorphic form as obtainable by the claimed process of the current invention is different to the polymorphic form of the material which can be obtained by published procedures. For this purpose two batches of Calcobutrol were prepared according to published procedures, and the corresponding XRPD spectra were compared with the XRPD spectra obtained from a Calcobutrol production batch prepared according to the invention. The synthesis of Calcobutrol according to the published procedures were performed starting with an aqueous Butrol solution (normally 17-22%) which is available on bulk.

General Production Procedure for the Production of an Aqueous Butrol Ligand Solution 2 kg of gadobutrol together with 0.8 kg of oxalic acid dihydrate were suspended in 14 L water and stirred for at least 3 hours at 80° C. (normally 3 to 5 hours). This was allowed to cool to 20° C. and further stirred for 60 minutes at 20° C. The gadolinium oxalate precipitated was filtered off and rinsed twice with 3 L water each time (~20 L ion exchanger eluate). An ion exchange column filled with cation exchange resin Amberlite 252 C was flushed with water until the eluate had reached a conductivity of <10 μS/cm (target pH>4.5 and <5.5). In this case a pH of pH 4.73 and a conductivity of 4.42 uS/cm were found. The aforesaid ion exchanger eluate (ca. 20 L) was fed onto the ion exchange column (feed rate 250-350 mL/min). This was then washed with 15 L water until the conductivity of the eluate was <5 μS/cm (measured values were pH 4.48 and 4.99 μS/cm). The ion exchange column was then slowly washed with a 1.4-1.7% aqueous ammonia solution (a 1.4% solution was used). The product-containing eluate fractions were collected (pH 11.01). The eluate was concentrated under vacuum at 64.4° C. until the solution had reached a density of 1.07 g/mL. 7.906 kg of a solution of pH 3.8 were obtained. A 127.13 g sample had previously been taken in order to determine pH, density and the butrol ligand content. After withdrawal of the sample, 7.7795 kg of solution remained with a butrol ligand content of 18.99% (measurement against external standard), which corresponded to a mass of 1.477 kg butrol.

For the following experiments an aqueous butrol ligand solution was prepared in a similar manner.

Example 5

Preparation of Calcobutrol According to Inorganic Chemistry 1997, 36, 6086-6093:

245.52 g of an 18% aqueous butrol solution (112 mmol, prepared as described above) was diluted with 330 ml water at room temperature. Then 10.99 g (112 mmol) calcium carbonate was added and the solution was heated at 80° C. for 2 h. It was cooled down to 22.6° C. and the solution was filtered and the filter residue was washed with 20 ml of water. The filtrate was freeze dried. The freeze dried powder (55.52 g) was suspended in 1315 ml ethanol (denaturated with methyl ethyl ketone) and was stirred at 50° C. for 1 h. For work-up the suspension was cooled down to 0° C. and the product was isolated by filtration. The product was washed with 395 ml ethanol (denaturated with methyl ethyl ketone) and then dried under vacuum until the mass was constant (at 60° C.).

Yield: 52.62 g (96.2% th.) of fine white powder was obtained.

Analytical Data:

Weight % water (Karl-Fischer): 3.47

Content ethanol: 610 ppm

Weight % methyl ethyl ketone: 0.00

Content Ca (Ion chromatography): 100.64

Figure 5:
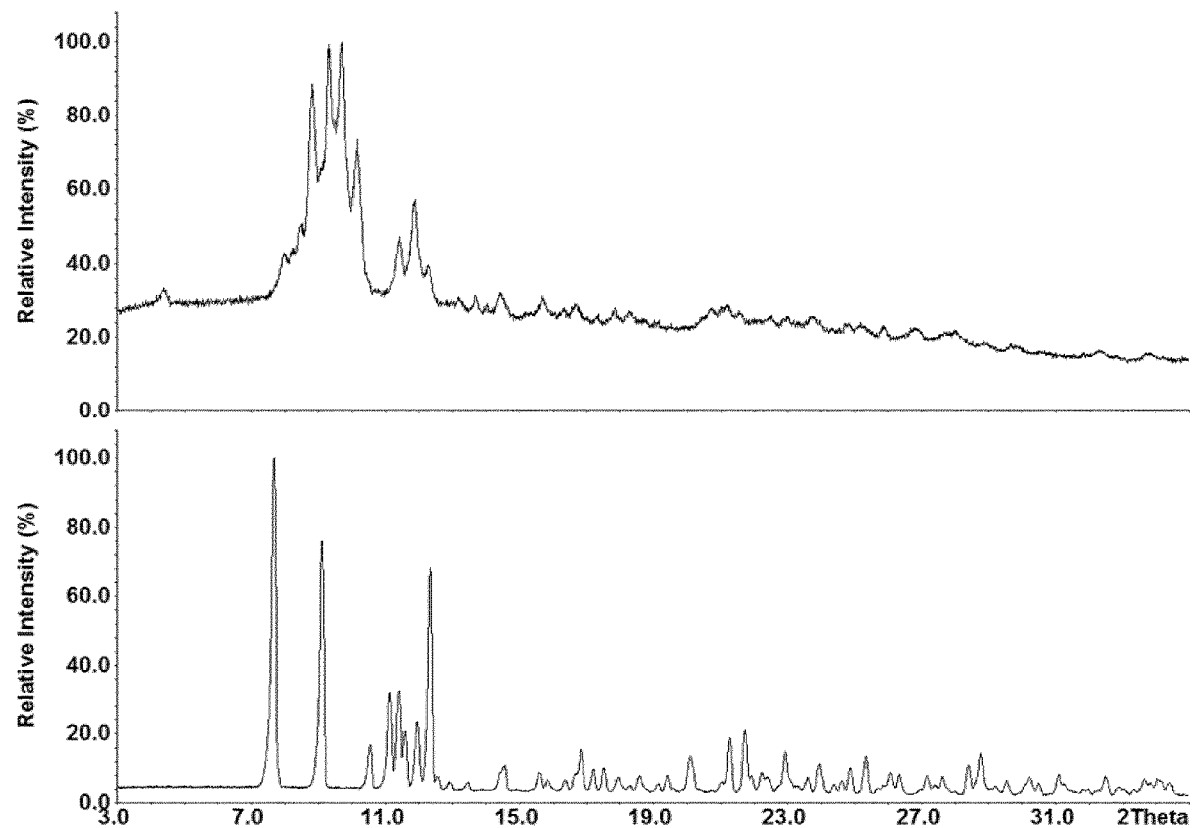
FIG. 5 shows the x-ray powder diffraction diagram of example 5 (upper diagram) in comparison to the x-ray powder diffraction diagram of a batch corresponding to modification A (lower diagram). This comparison clearly demonstrates that the polymorphic form corresponding to example 5, which was prepared according to the procedure described in Inorganic Chemistry 1997, 36, 6086-6093, is different from modification A as obtainable by the claimed process.

For the corresponding XRPD spectrum see FIG. 5.

Example 6

Preparation of Calcobutrol According to WO 2011/054827 A1:

245.54 g of an 18% aqueous butrol solution (50.45 g=112 mmol, prepared as described in example 1), was diluted with 208 ml water at room temperature. Then 11.34 g (112 mmol) calcium carbonate was added and the solution was heated at 90° C. for approximately 3 h. It was cooled down to room temperature (+20° C.). After this 5.06 g of freshly washed charcoal (Norit SX Plus) was added and the mixture was stirred for 1 h at room temperature. The solution was filtered and the filter residue (charcoal) was washed 3 times with each 50 ml water. The filtrate was reduced by distillation under vacuum at 80° C. to a certain volume which corresponds to 1.4 times of the original butrol ligand (1.4 times: 1.4×50.45 weight butrol ligand=70.6 ml). 505 ml ethanol (denaturated with methyl ethyl ketone) was added and the mixture was heated for 3 h under reflux. For work-up the suspension was cooled down to 20° C. and the product was isolated by filtration. The product was washed two times with each 50 ml ethanol (denaturated with methyl ethyl ketone) and then dried under vacuum until the mass was constant (at 70° C.).

Yield: 49.15 g (89.9 th.) of fine white powder was obtained.

Analytical Data:

Weight % water (Karl-Fischer): 2.54

Content ethanol: 200 ppm

Weight % methyl ethyl ketone: 0.00034

Content Ca (Ion chromatography): 100.80

Figure 6:
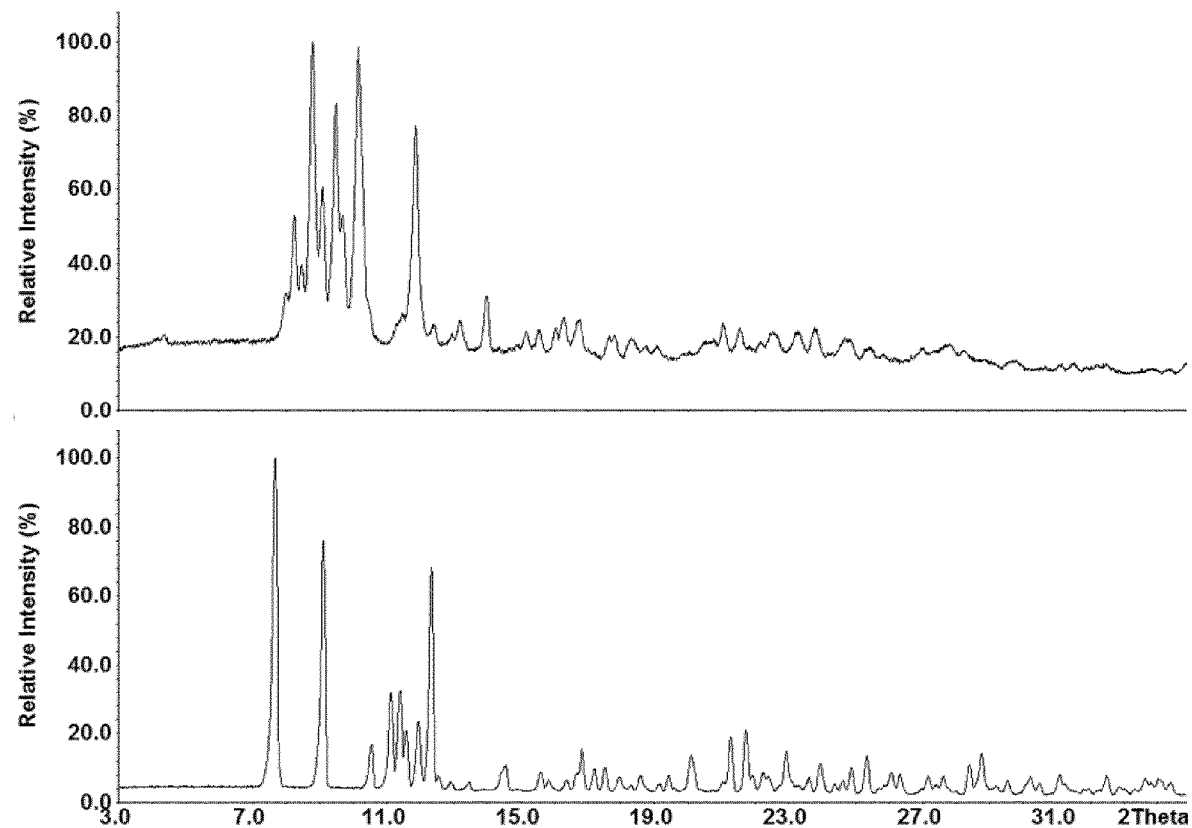
FIG. 6 shows the x-ray powder diffraction diagram of example 6 (upper diagram) in comparison to the x-ray powder diffraction diagram of a batch corresponding to modification A (lower diagram). This comparison clearly demonstrates that the polymorphic form corresponding to example 6, which was prepared according to the procedure described in WO 2011/054827 A1, is different from modification A as obtainable by the claimed process.

For the corresponding XRPD spectrum see FIG. 6.

Example 7

Hygroscopic Properties

The hygroscopic properties of three different samples of Calcobutrol were determined, one sample was prepared by the method described in Inorganic Chemistry 1997, 36, 6086-6093 (Example 5), one sample was prepared by the method described in WO2011/054827A1 (Example 6), and one sample was prepared by the method according to the present invention (Example 2).

2 g of each sample were exposed to ambient air (ca. 20° C., ca. 60% rel. humidity). The water content was measured by means of Karl-Fischer-Titration immediately after initial exposure (t=0), three hours (t=3 h), seven hours (t=7 h), and thirty one hours (t=31 h) after initial exposure.

Table 9 shows the increasing weight-% of water of the different sample over time. The Calcobutrol samples prepared according to methods described in prior art are much more hygroscopic than Calcobutrol prepared according to the process of the present invention.

TABLE 9

| Sample | weight-% water | | | |
| --- | --- | --- | --- | --- |
|  | t = 0 | t = 3h | t = 7h | t = 31h |
| Example 5 | 3.6% | 14.6% | 14.7% | 14.5% |
| Example 6 | 4.1% | 8.5% | 8.2% | 9.2% |
| Example 2 Modification A | 3.0% | 4.5% | 4.3% | 4.3% |

The invention claimed is:

1. A compound of formula (I) in a crystalline form of modification A

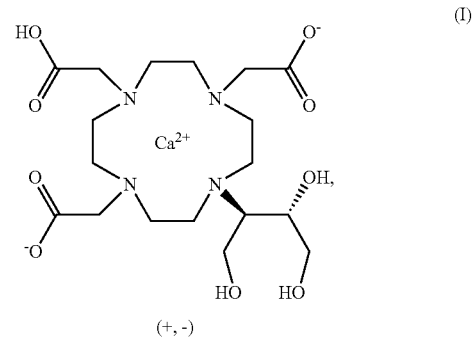

wherein an x-ray powder diffraction diagram of the compound shows peak maxima of a 2 theta angle at 7.6°, 9.1°, 11.1°, 11.3°, 11.9° and 12.3°.

2. A compound of formula (I) in a crystalline form of modification A

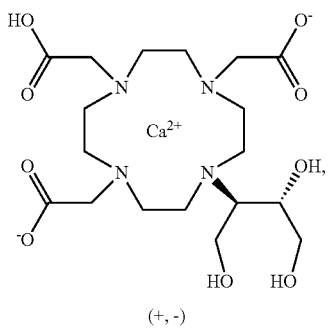

(I)

(+,-)

wherein the compound is a monohydrate with 2.0-2.5 weight % ethanol.

3. A compound of claim 2 having the formula (I) in the crystalline form of modification A

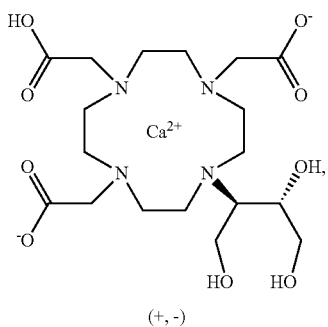

(I)

(+,-)

wherein an x-ray powder diffraction diagram of the compound shows peak maxima of a 2 theta angle at 7.6°, 9.1°, 11.1°, 11.3°, 11.9° and 12.3°.

4. A compound of formula (I) in a crystalline form of modification A produced by a method comprising:

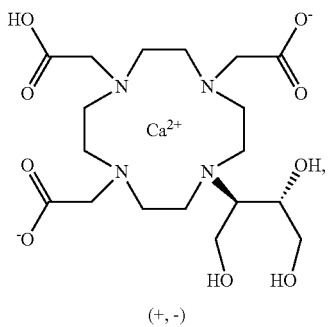

(I)

(+,-)

treating a solution of a dihydroxy-hydroxy-methylpropyl-tetraazacyclododecane-triacetic acid ligand to an acidic ion exchanger to bind the dihydroxy-hydroxy-methyl-propyl-tetraazacyclododecane-triacetic acid ligand to an acidic ion exchange column;

eluting the acidic ion exchange column having the bound dihydroxy-hydroxy-methylpropyl-tetraazacyclododecane-triacetic acid ligand with an aqueous basic solution to give an eluted solution of the dihydroxy-hydroxy-methylpropyl-tetraazacyclododecane-triacetic acid ligand;

complexing the eluted solution of the dihydroxy-hydroxy-methylpropyl-tetraazacyclododecane-triacetic acid ligand with $Ca^{2+}$;

adjusting a stoichiometric ratio of the dihydroxy-hydroxy-methylpropyl-tetraazacyclododecane-triacetic acid ligand and $Ca^{2+}$ to 1:1 to afford a calcium complex of dihydroxy-hydroxy-methylpropyl-tetraazacyclodode-cane-triacetic acid;

crystallizing the calcium complex of dihydroxy-hydroxy-methylpropyl-tetraazacyclododecane-triacetic acid from an aqueous ethanol solution with a water content of from 9 to 11 weight % of water to give a crystallized calcium complex of dihydroxy-hydroxy-methylpropyl-tetraazacyclododecane-triacetic acid; and isolating and drying the crystallized calcium complex of dihydroxy-hydroxy-methylpropyl-tetraazacyclodode-cane-triacetic acid to afford the compound of formula (I) in the crystalline form of modification A, wherein an x-ray powder diffraction diagram of the compound shows peak maxima of a 2 theta angle at 7.6°, 9.1°, 11.1°, 11.3°, 11.9° and 12.3°.

5. The compound of the formula (I) of claim 1, wherein the compound has a purity of greater than or equal to 99.0%.

6. The compound of the formula (I) of claim 1, wherein the compound has a purity of greater than or equal to 99.7%.

7. A galenical formulation of Gadobutrol, the formulation comprising:

Gadobutrol dissolved in a suitable pharmaceutical solvent; and a calcium complex of dihydroxy-hydroxy-methylpropyl-tetraazacyclododecane-triacetic acid in a crystalline form of modification A dissolved in the suitable pharmaceutical solvent, wherein an x-ray powder diffraction diagram of the crystalline form of the modification A of the calcium complex of dihydroxy-hydroxy-methylpropyl-tetraaza-cyclododecane-triacetic acid shows peak maxima of a 2 theta angle at 7.6°, 9.1°, 11.1°, 11.3°, 11.9° and 12.3°.

8. The galenical formulation of Gadobutrol of claim 7, wherein the calcium complex of dihydroxy-hydroxy-methylpropyl-tetraazacyclododecane-triacetic acid has a purity of greater than or equal to 99.0%.

* * * * *

UNITED STATES PATENT AND TRADEMARK OFFICE
CERTIFICATE OF CORRECTION

PATENT NO. : 10,793,532 B2  
APPLICATION NO. : 16/336217  
DATED : October 6, 2020  
INVENTOR(S) : Platzek et al.

Page 1 of 1

It is certified that error appears in the above-identified patent and that said Letters Patent is hereby corrected as shown below:

In the Specification  
In Column 4, Line 10, delete "in on" and insert -- of on --, therefor.  
In Column 4, Line 62, delete "9% and 11%," and insert -- $\geq$9% and $\leq$11%, --, therefor.  
In Column 11, Line 26, delete "9 and 11" and insert -- $\geq$9 and $\leq$11 --, therefor.  
In Column 12, Line 18, delete "5,000" and insert -- $\leq$5,000 --, therefor.  
In Column 12, Line 36, delete "12 weight %)" and insert -- ($\geq$ 12 weight %) --, therefor.  
In Column 14, Line 21, delete "3° 20 35°" and insert -- 3°$\leq$2θ$\leq$35° --, therefor.  
In Column 15, Line 26, delete "3.47" and insert -- 3.47 % --, therefor.  
In Column 15, Line 29, delete "0.00" and insert -- 0.00 % --, therefor.  
In Column 15, Line 30, delete "100.64" and insert -- 100.64 % --, therefor.  
In Column 15, Line 59, delete "(89.9" and insert -- (89.9 % --, therefor.  
In Column 15, Line 61, delete "2.54" and insert -- 2.54 % --, therefor.  
In Column 15, Line 65, delete "0.00034" and insert -- 0.00034 % --, therefor.  
In Column 15, Line 66, delete "100.80" and insert -- 100.80 % --, therefor.

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*